United States Patent
Veis

(10) Patent No.: US 12,303,424 B2
(45) Date of Patent: May 20, 2025

(54) ADJUSTABLE SLEEP APNEA ORAL APPLIANCE FOR USE WITH ORTHODONTIC BRACES

(71) Applicant: R.I.P., LLC, Chatsworth, CA (US)

(72) Inventor: Rob Veis, Malibu, CA (US)

(73) Assignee: R.I.P., LLC, Chatsworth, CA (US)

( * ) Notice: Subject to any disclaimer, the term of this patent is extended or adjusted under 35 U.S.C. 154(b) by 0 days.

(21) Appl. No.: 18/832,656

(22) PCT Filed: Sep. 5, 2023

(86) PCT No.: PCT/US2023/073495
§ 371 (c)(1),
(2) Date: Jul. 24, 2024

(87) PCT Pub. No.: WO2024/050568
PCT Pub. Date: Mar. 7, 2024

(65) Prior Publication Data
US 2025/0099292 A1    Mar. 27, 2025

Related U.S. Application Data

(60) Provisional application No. 63/403,400, filed on Sep. 2, 2022.

(51) Int. Cl.
*A61C 7/28* (2006.01)
*A61F 5/56* (2006.01)

(52) U.S. Cl.
CPC .............. *A61F 5/566* (2013.01); *A61C 7/28* (2013.01)

(58) Field of Classification Search
CPC .... A61C 7/28; A61C 7/08; A61C 7/36; A61F 5/566
See application file for complete search history.

(56) References Cited

U.S. PATENT DOCUMENTS

| 9,545,332 | B2* | 1/2017 | Luco | A61F 5/566 |
| 9,949,867 | B2* | 4/2018 | Veis | A61F 5/566 |
| 11,534,331 | B2* | 12/2022 | Veis | A61C 7/36 |

(Continued)

OTHER PUBLICATIONS

International Search Report and Written Opinion for International Patent Application No. PCT/US2023/073495, dated Feb. 28, 2024.

*Primary Examiner* — Ralph A Lewis
(74) *Attorney, Agent, or Firm* — LOZA & LOZA LLP; Michael Fedrick

(57) ABSTRACT

An oral appliance for treating snoring and/or apnea including an upper appliance portion and a lower appliance portion. The upper appliance portion has an upper base which extends over anterior teeth of a user's upper jaw and two orthodontic wires, one extending from each lateral side of the upper base portion, while the lower appliance portion has a lower base portion which extends over anterior teeth of a user's lower jaw and two orthodontic wires, one extending from each lateral side of the upper base portion. A lingual portion of each wire extends posteriorly from a proximal end on the lingual side of a user's teeth, around the rearmost tooth of the user, and then extends anteriorly along the buccal side of the user's teeth to a distal end of the wire, with the wire positioned between the brackets and the gum line of a user when worn.

12 Claims, 11 Drawing Sheets

(56) References Cited

U.S. PATENT DOCUMENTS

| | | | |
|---|---|---|---|
| 2014/0076332 A1* | 3/2014 | Luco | A61F 5/566 |
| | | | 128/848 |
| 2016/0015556 A1* | 1/2016 | Luco | A61F 5/566 |
| | | | 128/848 |
| 2017/0135850 A1* | 5/2017 | Veis | A61F 5/566 |
| 2018/0185188 A1* | 7/2018 | Lamberg | A61F 5/566 |
| 2018/0353321 A1* | 12/2018 | Veis | A61C 7/36 |
| 2019/0000662 A1* | 1/2019 | Veis | A61F 5/56 |

* cited by examiner

ADJUSTABLE SLEEP APNEA ORAL APPLIANCE FOR USE WITH ORTHODONTIC BRACES

CROSS-REFERENCE TO RELATED APPLICATIONS

This application is the U.S. national stage of International Patent Application No. PCT/US2023/073495, filed on Sep. 5, 2023, which claims the benefit of priority under 35 U.S.C. § 119(e) from U.S. Patent Application No. 63/403,400, filed Sep. 2, 2022. The disclosures of the foregoing applications are incorporated herein by reference in their entireties.

INTRODUCTION/BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

Subjects are generally at greater risk for sleep apnea if they are overweight or have conditions such as diabetes, hypertension, or chronic nasal congestion. There are a variety of factors, however, which can lead to sleep apnea, including a narrow maxilla and/or mandible in a subject, which reduces intraoral air volume and tends to force the tongue back into the posterior airway space, leading to obstructive sleep apnea during sleep.

Orthodontics is a field of dentistry which focuses on the repositioning of a subject's teeth and jaws for therapeutic, aesthetic or other reasons, for example due to the "overcrowding" of a subject's teeth. Orthodontic methods typically require a subject to make continuous use of mechanical devices, such as braces or a dental appliance, for a period of time in order to achieve results. The use of braces precludes the concurrent use of currently available oral appliances for treating sleep apnea. There remains a need therefore for improved devices and methods for treating sleep apnea in subjects who are undergoing orthodonture and who experience sleep apnea.

SUMMARY

The present adjustable sleep appliance is designed for use with orthodontic braces and generally comprises an upper appliance portion 100, for use on the maxillary dentition of a user who wears braces, and a lower appliance portion 200, for use on mandibular dentition of the user. The upper appliance portion 100 includes an upper base portion 150 which includes an upper right side wire 172, an upper left side wire 174, an upper receptacle 160, and a downwardly extending projection 400. The upper base portion 150 further has a right side 152, a left side 154, an anterior side 151, a posterior side 153, an upper side 156, and a lower side 158. The upper right side wire 172 and upper left side wire 174 each have a proximal end 71, a distal end 73, a lingual wire portion 76, a buccal wire portion 78, and a medial portion 75, where:

(i) the proximal end 71 of the upper right side wire 172 is attached to the right side 152 of the upper base portion 150, and the proximal end 71 of the upper left side wire 174 is attached to the left side 154 of the upper base portion 150;

(ii) the lingual wire portion 76 of the upper right side wire 172 extends posteriorly from the proximal end 71 to the medial portion 75, the medial portion 75 of the upper right side wire 172 extends laterally, and the buccal wire portion 78 of the upper right side wire 172 extends from the medial portion 75 anteriorly to the distal end 73; and the lingual wire portion 76 of the upper left side wire 174 extends posteriorly from the proximal end 71 to the medial portion 75, the medial portion 75 of the upper left side wire 174 extends laterally, and the buccal wire portion 78 of the upper left side wire 174 extends from the medial portion 75 anteriorly to the distal end 73; and (iii) the upper right side wire 172 and upper left side wire 174 are adapted to fit between brackets of orthodontic braces affixed to teeth of the user of the appliance 10 and gum tissue of the user.

The upper receptacle 160 has an upper surface 66 and includes a thermoplastic material 90. The downwardly extending projection 400 has a proximal end 402, a distal end 404, an anterior surface 401, and a posterior surface 403, and is attached to and extends downwardly from the lower side 158 of the upper base portion 150.

The lower appliance portion 200 has a lower base portion 250 which includes a lower right side wire 272, a lower left side wire 274, and a lower receptacle 260. The lower base portion 250 further includes a right side 252, a left side 254, an anterior side 251, a posterior side 253, an upper side 256, and a lower side 258. The lower receptacle 260 has a lower surface 68 and includes a thermoplastic material 90. The lower right side wire 272 and lower left side wire 274 each have a proximal end 71, a distal end 73, a lingual wire portion 76, a buccal wire portion 78, and a medial portion 75, where:

(i) the proximal end 71 of the lower right side wire 272 is attached to the right side 252 of the lower base portion 250, and the proximal end 71 of the lower left side wire 274 is attached to the left side 254 of the lower base portion 250;

(ii) the lingual wire portion 76 of the lower right side wire 272 extends posteriorly from the proximal end 71 to the medial portion 75, the medial portion 75 of the lower right side wire 272 extends laterally, and the buccal wire portion 78 of the lower right side wire 272 extends from the medial portion 75 anteriorly to the distal end 73; and the lingual wire portion 76 of the lower left side wire 274 extends posteriorly from the proximal end 71 to the medial portion 75, the medial portion 75 of the lower left side wire 274 extends laterally, and the buccal wire portion 78 of the lower left side wire 274 extends from the medial portion 75 anteriorly to the distal end 73; and (iii) the lower right side wire 272 and lower left side wire 274 are adapted to fit between brackets of orthodontic braces affixed to teeth of the user of the appliance 10 and gum tissue of the user, and is adapted to fit between brackets of orthodontic braces affixed to teeth of the user of the appliance 10 and gum tissue of the user.

The anterior surface 401 of the projection 400 is adapted to contact the posterior side 253 of the lower base portion 250 when the appliance is in use, thereby limiting anterior movement of the upper appliance portion 100 with respect to the lower appliance portion 200. In addition, the upper right side wire 172, upper left side wire 174, lower right side wire 272, and lower left side wire 274 preferably can be elastically deformed and are adapted to contact a user's teeth under tension.

The thermoplastic material of the appliance can be reversibly deformed in order to accommodate changing tooth positions of the teeth of the user. In one embodiment, the upper base portion 150 and lower base portion 250 can be formed completely from a thermoplastic material. Alternatively, the upper base portion 150 and lower base portion 250 can comprise both a hard plastic material portion and a thermoplastic material portion for contact with the user's teeth.

Preferably, one or more of the upper right side wire 172, upper left side wire 174, lower right side wire 272, and/or lower left side wire 274 include a clasp. The clasp is a projection or flange which extends medially from the buccal wire portion 78 or laterally from the lingual wire portion 76 and is adapted to extend over an occlusal surface of a tooth of the user.

In one embodiment, the lower appliance portion 200 can further include an insert 300 having a right side 312, a left side 314, an anterior side 311, a posterior side 313, an upper side 316, and a lower side 318. The insert has a receiving portion in the lower base portion 250 and is configured to be secured to the receiving portion 280. The anterior side 311 of the insert 300 and the posterior side 253 of the lower appliance portion 250 can be provided with mutually fitting locking elements, such as tongue-and-groove locking elements, in order to secure the insert 300 to the receiving portion 280.

This embodiment can include a plurality of inserts 300, where the posterior side 313 of each of the plurality of inserts extends posteriorly by a different distance when retained in the receiving portion 280, and each of the plurality of inserts is reversibly securable to the lower appliance portion 250. In this way, an anterior-posterior positioning of the upper appliance portion 100 can be adjusted with respect to the lower appliance portion 200 through the use of the inserts, since they extend posteriorly by different distances. The distance by which each of the inserts extends posteriorly can differ by between 0.5 mm and 1.0 mm, for example.

The present appliance can be used in the treatment of snoring or sleep apnea. In such a treatment method, the present appliance is applied to (worn by) a subject in need thereof. This method preferably further includes the steps of:
  (a) heating the upper appliance portion in order to soften the thermoplastic material of the upper appliance portion and taking an impression of the subject's anterior maxillary dentition;
  (b) heating the lower appliance portion in order to soften the thermoplastic material of the lower appliance portion and taking an impression of the subject's anterior mandibular dentition;
  (c) repeating steps (a) and (b) every 1-3 days.

Figure 1:
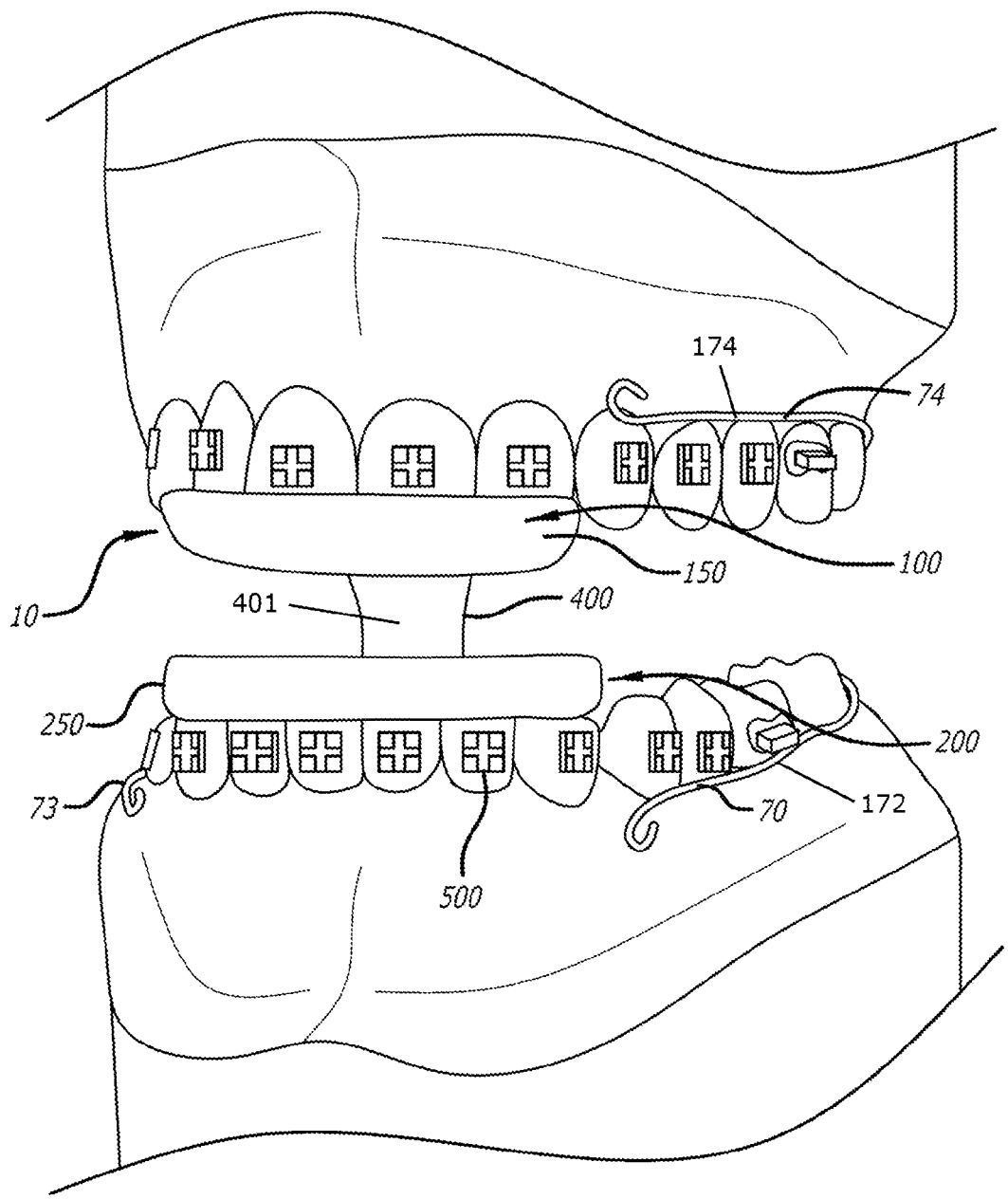
FIG. 1 is a front, left perspective view of an embodiment of the present appliance on a model of a subject's teeth.

The reference numbers in the figures have the following meanings:

| Component | Subcomponent | Reference Number |
| --- | --- | --- |
| Appliance | | 10 |
| Appliance portion | | 40 |
| | Right side | 42 |
| | Left side | 44 |
| | Anterior portion | 41 |
| | Posterior portion | 43 |
| Base | | 50 |
| | Right side | 52 |
| | Left side | 54 |
| | Anterior side | 51 |
| | Posterior side | 53 |
| | Upper side | 56 |
| | Lower side | 58 |
| | Receptacle | 60 |
| | Receptacle wall | 65 |
| | Receptacle upper surface | 66 |
| | Receptacle lower surface | 68 |
| Wire | | 70 |
| | Right side wire | 72 |
| | Left side wire | 74 |
| | Proximal end | 71 |
| | Distal end | 73 |
| | Medial portion | 75 |
| | Lingual wire portion | 76 |
| | Buccal wire portion | 78 |
| | Posterior wire portion | 79 |
| | Anterior wire portion | 81 |
| | Occlusal clasp | 83 |
| Thermoplastic material | | 90 |
| | Thermoplastic material outer surface | 96 |
| Upper appliance portion | | 100 |
| | Base portion | 150 |
| | Right side | 152 |
| | Left side | 154 |
| | Anterior side | 151 |
| | Posterior side | 153 |
| | Upper side | 156 |
| | Lower side | 158 |
| | Upper receptacle | 160 |

-continued

| Component | Subcomponent | Reference Number |
|---|---|---|
| | Upper right side wire | 172 |
| | Upper left side wire | 174 |
| Lower appliance portion | | 200 |
| | Base | 250 |
| | Right side | 252 |
| | Left side | 254 |
| | Anterior side | 251 |
| | Posterior side | 253 |
| | Upper side | 256 |
| | Lower side | 258 |
| | Lower receptacle | 260 |
| | Lower right side wire | 272 |
| | Lower left side wire | 274 |
| | Receiving portion | 280 |
| | Connector mating portion | 289 |
| Insert | | 300 |
| | Plurality of inserts | 301, 302, 303 |
| | Right side | 312 |
| | Left side | 314 |
| | Anterior side | 311 |
| | Posterior side | 313 |
| | Contact portion | 315 |
| | Upper side | 316 |
| | Lower side | 318 |
| | Base-contacting surface | 319 |
| Connectors | | 350 |
| | Connector attachment end/portion | 351 |
| Downwardly extending projection | | 400 |
| | Proximal end | 402 |
| | Distal end | 404 |
| | Anterior surface | 401 |
| | Posterior surface | 403 |
| Brackets | | 500 |

DETAILED DESCRIPTION

Definitions

As used herein, the following terms and variations thereof have the meanings given below, unless a different meaning is clearly intended by the context in which such term is used.

"Above" refers to the relative position of the present appliance or a component thereof which is closer to or is toward an upper portion of a subject's body when the appliance is being used, while "below" refers to the opposite relative position of the present appliance or a component thereof, i.e. being closer to or in the direction of a lower portion of a subject's body when the appliance is being used "Anterior" and "anteriorly" mean in the direction of or toward or adjacent the front portion (opening) of a subject's mouth when the present appliance is worn by a subject.

"Apnea" and "sleep apnea" refer to a temporary cessation of breathing and/or to instances of shallow or infrequent breathing during sleep, generally caused by a blockage of a subject's airway (referred to as obstructive sleep apnea).

"Braces" refer to dental braces, i.e., to a series of brackets and wires used to reposition teeth and/or reshape jaws.

"Brackets" are mechanical components which are anchored to a subject's tooth, generally by a bonding material, and which are connected to wires which distribute force among a subject's bracketed teeth in the course of orthodontic treatment. Brackets are usually fixed in place on the buccal side of a subject's teeth.

"Buccal" means in the direction of or toward a subject's cheek. In relation to a subject's teeth, this refers to the side of the teeth facing the cheek.

"Clasp" refers to a mechanical portion of the present appliance which grips and helps retain the appliance on a user's teeth when in use.

"Downward" and "downwardly" mean in the direction of or toward a lower portion of a subject's body when the present appliance is being worn. "Upward" and "upwardly" mean in the opposite direction, i.e. in the direction of or toward an upper portion of a subject's body.

"Hard plastic" refers to a polymer material which is not elastically deformable, such as poly(methyl methacrylate) (also known as acrylic), polycarbonate, acrylonitrile butadiene styrene (ABS) and others. The hard plastics used for the present appliance are non-toxic and compatible for use in a human subject's mouth. Hard plastics used in orthodontic applications are known to the art and can be used in the present appliance.

"Horizontal," with respect to the present appliance, refers to disposition in a plane approximately parallel to a subject's bite surface, i.e., within 15 degrees of such a plane, which is approximately perpendicular to the sagittal and/or the coronal plane of a subject.

"Laterally" refers to a position or direction toward the right or left side of the present appliance, and/or toward an outer portion of the mouth of a subject when the appliance is worn by the subject, i.e., buccally.

"Lingual" means in the direction of, toward, or adjacent to a subject's tongue. In relation to a subject's teeth, this refers to the side of the front teeth facing the tongue, i.e., facing inwardly.

"Lower" refers to the relative position of a component in the present device which is closer to or toward a lower portion of a subject's body when the device is being used.

"Mandibular" refers to the lower jaw.

"Maxillary" refers to the upper jaw.

"Medially" refers to a position or direction toward a middle portion of the present appliance, and/or toward an inner portion of the mouth of a subject when the appliance is worn by the subject, i.e., lingually.

"Occlusal surface" refers to the biting surfaces of teeth.

"Orthodontic" refers to a device or component thereof which repositions the teeth and/or jaw(s) of a subject.

"Orthodontic wire" refers to a length of metal wire of the type used in orthodontic treatment.

"Posterior" and "posteriorly" mean in the direction of or toward or adjacent the rear portion of a subject's mouth when the appliance is worn by a subject.

"Right" refers to the right side of the present appliance when in use, i.e., right of the center sagittal plane of a subject, from the perspective of the subject. "Left" refers to the other side, i.e., the left side of the appliance.

"Subject" refers to a user of the present appliance, usually a human user.

"Thermoplastic" and "soft plastic" refer to a material, generally a polymer material, which is elastically deformable at temperature between room temperature and the boiling point of water. Such plastics may be softened, such as by heat, and then re-hardened, such as by cooling, in a reversible physical process. One such material is THERMACRYL (a polymer available from Airway Management, Inc., Farmers Branch, TX), while another is ethylene vinyl acetate (EVA). The thermoplastic materials used in some components of the present appliance retain their shape at 100° F. and preferably become soft (deformable) at a temperature of 212° F. or below.

"Upper" refers to the relative position of a component in the present appliance which is closer to or toward an upper portion of a subject's body when being used.

"Vertical" refers to a plane or direction which is perpendicular to a horizontal plane or direction.

The terms "above," "below," "between," and other terms of relative position or orientation as used herein refer to a relative position of one layer with respect to other layers. As such, one layer deposited or disposed above or below another layer may be directly in contact with the other layer or may have one or more intervening layers, unless described otherwise herein.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. Ranges which are described as being "between" two values include the indicated values.

Appliance and Method of Use

The present sleep appliance is designed to be worn by subjects who wear braces. When braces are worn, brackets are generally secured to an outer surface of a subject's teeth as anchors for exerting and distributing force through a wire. A bracket is usually secured on the buccal surface of a tooth, and a wire (archwire) is then mechanically connected to the bracket. The wire extends between the bracket and other brackets on other teeth, either other upper teeth or other lower teeth as the case may be, exerting and distributing force between the teeth. Brackets are typically placed in a relatively central portion of the area of tooth which is outside the gingiva (gum tissue), i.e., such that there is space between a subject's gingiva and the bracket.

The present appliance 10 comprises an upper appliance portion 100 and a lower appliance portion 200, and the appliance portions 40 each comprise a base 50 for receiving a user's anterior teeth (such as the incisors), namely upper appliance portion base 150 and lower appliance portion base 250, respectively. The base portions 50 have a right side 52, a left side 54, an anterior side 51, a posterior side 53, an upper side 56, and a lower side 58 and include a receptacle 60 for contacting and/or receiving the outer surfaces of anterior teeth of a user of the appliance 10. The upper base portion 150 is positioned in the anterior portion 41 of the upper appliance portion 100, and the lower base 250 is positioned in the anterior portion 41 of the lower appliance portion 200. The upper base portion 150 and lower base 250 cooperate to limit forward movement of a user's upper jaw.

Specifically, the upper appliance portion 100 includes an upper base portion 150 with a right side 152, left side 154, anterior side 151, posterior side 153, upper side 156, and lower side 158, with an upper receptacle 160 positioned on the upper side 156 of the upper base portion for receiving a user's upper (maxillary) teeth. Extending from the right side 152 is an upper right side wire 172, while extending from the left side 154 is an upper left side wire 174. The lower appliance portion 200 similarly includes a lower base portion 250 with a right side 252, left side 254, anterior side 251, posterior side 253, upper side 256, and lower side 258, with a lower receptacle 260 on the lower side 258 of the lower base portion for receiving a user's mandibular teeth. Extending from the right side 252 is a lower right side wire 272, while extending from the left side 254 is a lower left side wire 274.

The upper receptacle 160 of the upper appliance base 150 extends across and contacts or receives at least an incisal portion of a user's anterior teeth on the upper jaw, including the incisal surfaces, covering between 2 and 6 teeth for example, and the lower receptacle 260 likewise extends across and receives at least an incisal portion of a user's mandibular anterior teeth, covering for example between 2 and 6 teeth, with at least a portion of 3 or 4 teeth preferably being covered by the receptacle 60 of each of the bases 50. The receptacles 60 preferably cover no more than one third of the anterior and posterior surfaces (i.e., the buccal and lingual surfaces) of the incisal portion of a user's teeth, i.e., the upper one-third of mandibular teeth and the lower one-third of maxillary teeth.

The receptacle portions 60 of each base 50 can be formed from a hard plastic material and configured to accommodate a user's teeth in the different positions that they are expected to be located during the course of an orthodontic treatment. However, the receptacles 60 preferably comprises a thermoplastic (soft plastic) material, such as a THERMACRYL, laminate (an acrylic based thermoplastic material). Such thermoplastic materials retain their shape when used by a subject, and thus preferably remain solid at least at body temperatures, but preferably also remain solid at somewhat higher temperatures, such as at 110° F., 120° F., or higher. Thermoplastic materials are however deformable at higher temperatures, such as the temperature of boiling water (212° F.) or less, and are preferably made plastic by being placed in boiling water. While the plastic material of the receptacle is in such a deformable state, the user can impress the material with their upper or lower dentition, as the case may be, and once the material has cooled it will thereby conform to the shape of the user's dentition, creating a stable support (i.e., a positive seat) for the user's teeth in the receptacle 60 and helping to maintain the base 50 stably on the user's dentition.

Figure 9:
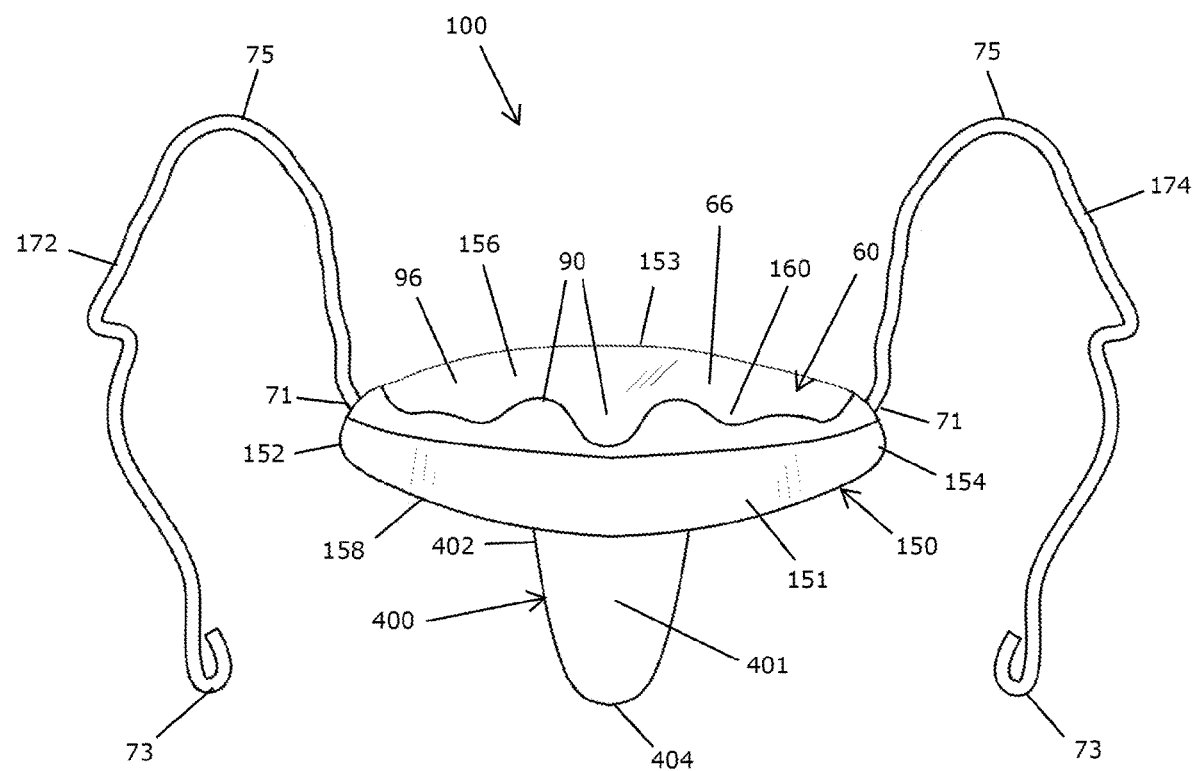
FIG. 9 is a front perspective view of an embodiment of an upper appliance portion of the present appliance.
Figure 10:
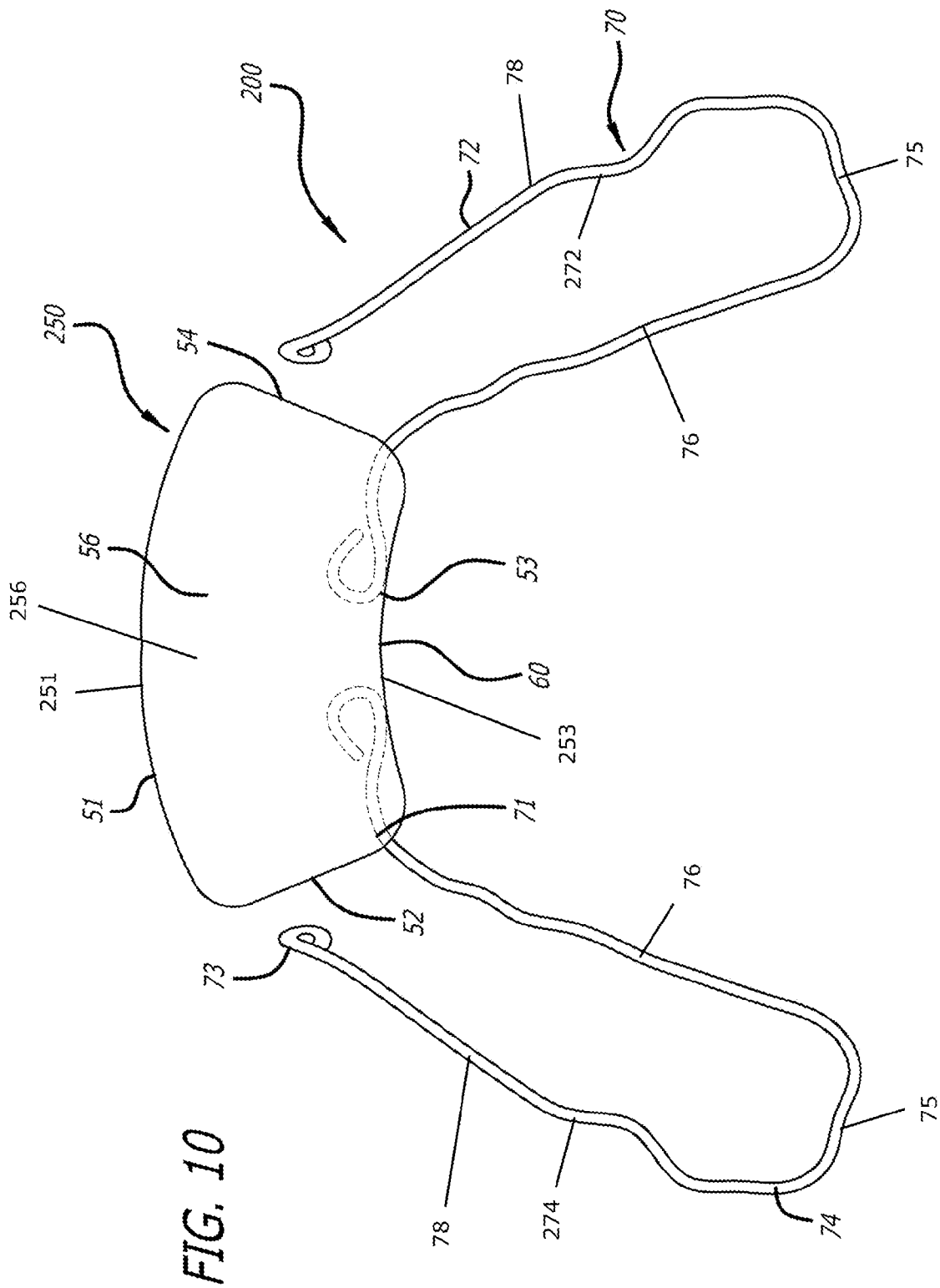
FIG. 10 is a top plan view of an embodiment of the lower appliance portion of the present appliance.
Figure 11:
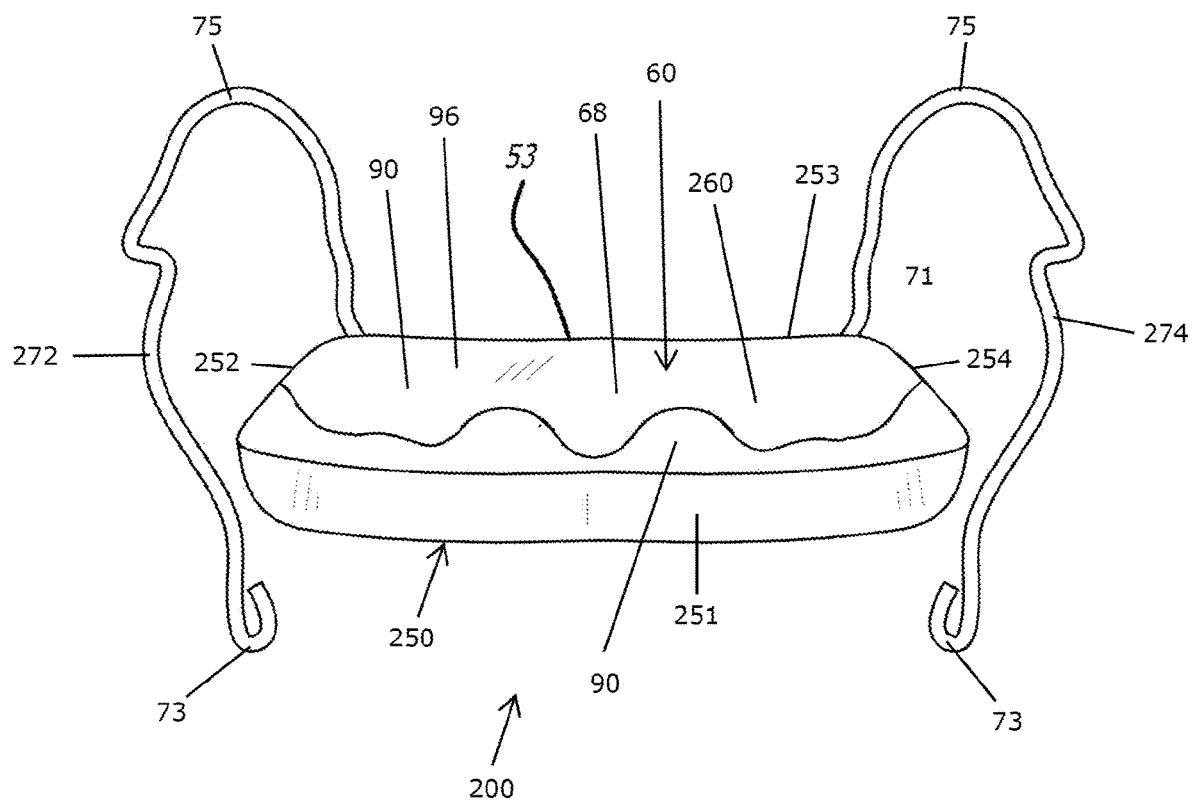
FIG. 11 a front perspective view of an embodiment of a lower appliance portion of the present appliance.

When the receptacle 160 of the upper base portion 150 includes a thermoplastic material 90, the thermoplastic material is present on an upper surface 66 of the receptacle, as can be seen in FIG. 9, for example. In this way, the outer surface 96 of the thermoplastic material 90 can receive an impression from a user's upper teeth when the material is softened. Likewise, when the receptacle 260 of the lower base portion 250 includes a thermoplastic material 90, the thermoplastic material is present on a lower surface 68 of the receptacle, as can be seen in FIG. 11. In this way, the outer surface 96 of the thermoplastic material 90 can receive an impression from a user's lower teeth when the material is softened. The use of thermoplastic materials 90 provide a better fit with a user's anterior teeth, and thus a more stable seat for the appliance 10 in the user's mouth. Preferably, the receptacles 60 of the upper and lower bases 50 receive impressions from the teeth of a user of the present appliance on a regular basis, such as every day, or every 2 or 3 days, in order to accommodate changes in the positioning of the user's teeth, which steadily change in position during the course of orthodontic treatment. In an advantageous embodiment, the bases 50 of the present appliance can be formed from a single material, preferably a thermoplastic material. Such materials also preferably can be 3D printed in order to facilitate manufacturing.

Extending from each lateral side of the base 50 of an appliance portion 40 is a wire 70, i.e., a right side wire 72 and a left side wire 74. A proximal end 71 of each wire is fixed to a respective side of the base 50 to which it is attached. Preferably, the proximal end 71 of a wire is embedded in a polymer material forming the base 50, which can be accomplished for example by heating the polymer material and then inserting the proximal end 71 of the wire 70 into the softened plastic. A lingual portion 76 of each wire 70 then extends posteriorly from the proximal end 71 of the wire on the lingual side of a user's mouth when worn by the user. The lingual portion 76 of each wire 70 is configured to be touching or directly adjacent to the lingual side of the user's teeth and away from the gingiva (gums). A medial portion 75 of the wire 70 extends around the posterior surface of the rearmost (most posterior) tooth of the subject on the right side or the left side of the subject's mouth, as the case may be, and is bent around the rearmost tooth so that a buccal portion 78 of the wire then extends anteriorly along the buccal side of the user's teeth. The buccal portion 78 of each wire 70 is configured to be touching or directly adjacent to the buccal side of the subject's teeth between the brackets and the gum line. The buccal portion 78 extends anteriorly to a distal end 73 of the wire. The distal end 73 is preferably capped, blunted, or otherwise protected so that the user is not irritated or injured by the distal end of the wire. In the illustrated embodiments, the distal end of the wire is formed into a loop so that the rounded portion of the loop is positioned at the distal end of the wire 70. The lingual portion 76 and buccal portion 78 of each wire are each preferably shaped to conform to the shape of the teeth to which they are adjacent, at least over a portion of the wire 70, so that the appliance 10 is better retained on the user's dentition.

Figure 2:
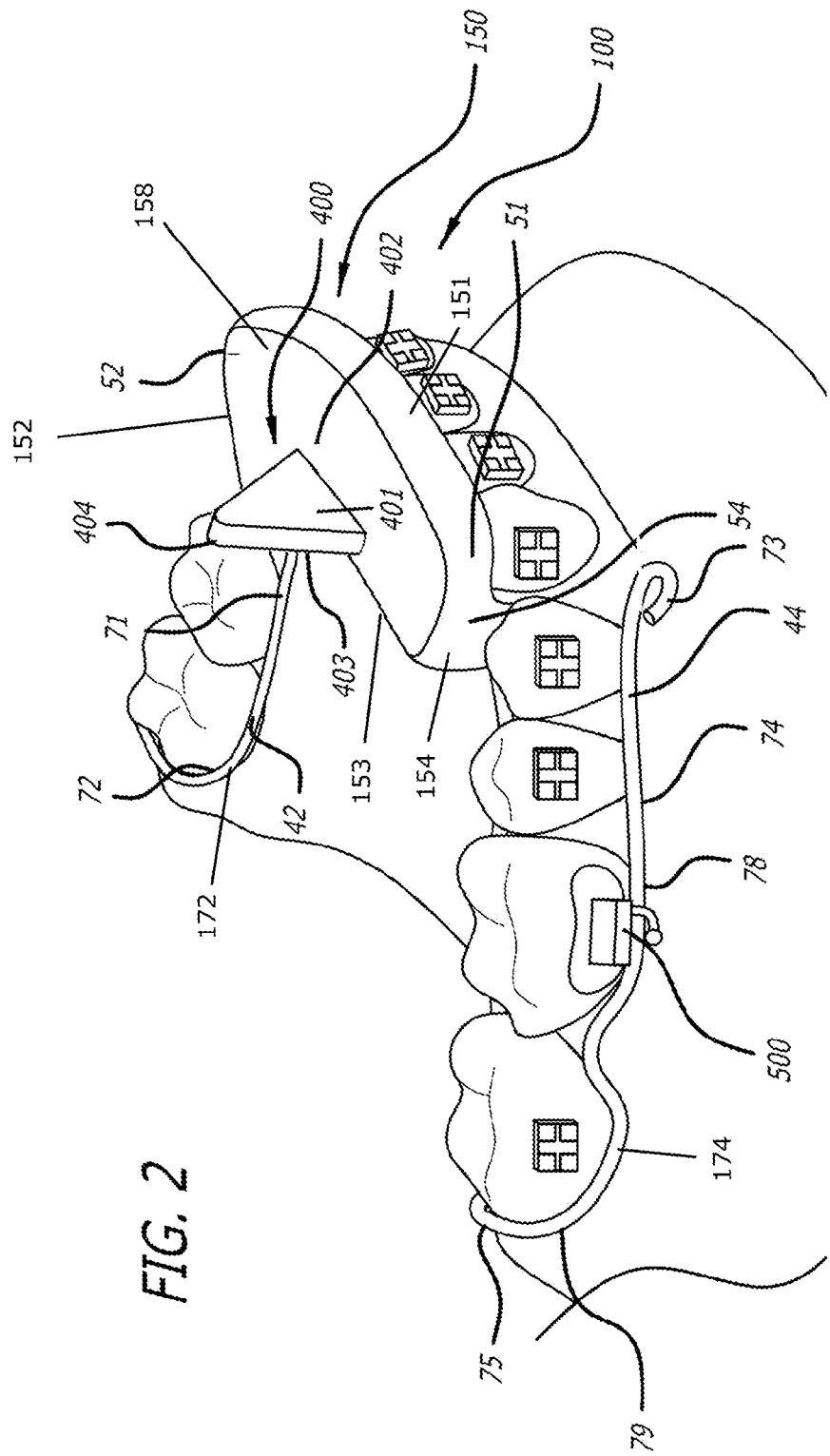
FIG. 2 is a front, left perspective view of an embodiment of the upper appliance portion of the present appliance on a model of a subject's teeth.
Figure 3:
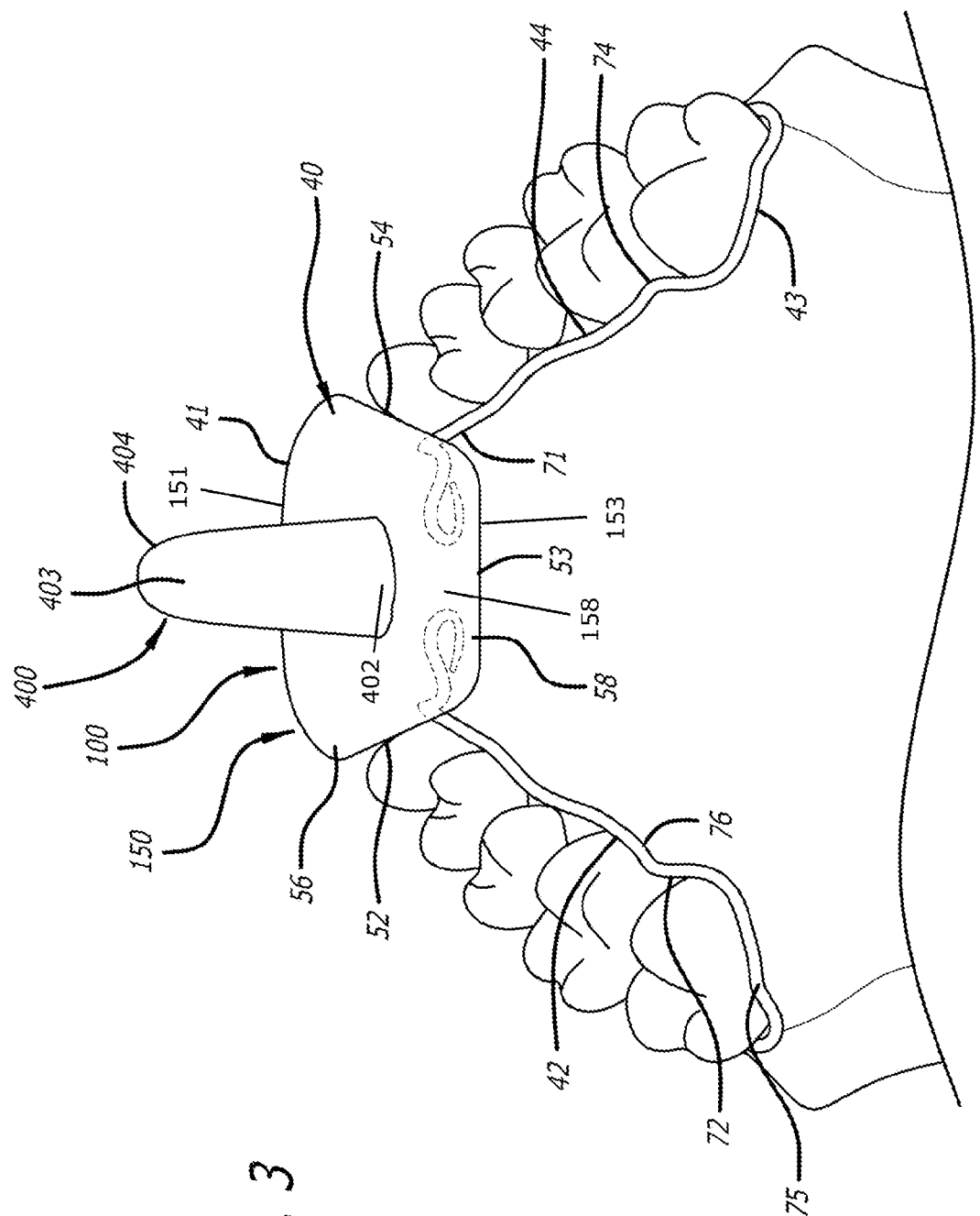
FIG. 3 is a rear view of the upper appliance portion of an embodiment of the present appliance on a model of a subject's teeth.
Figure 4:
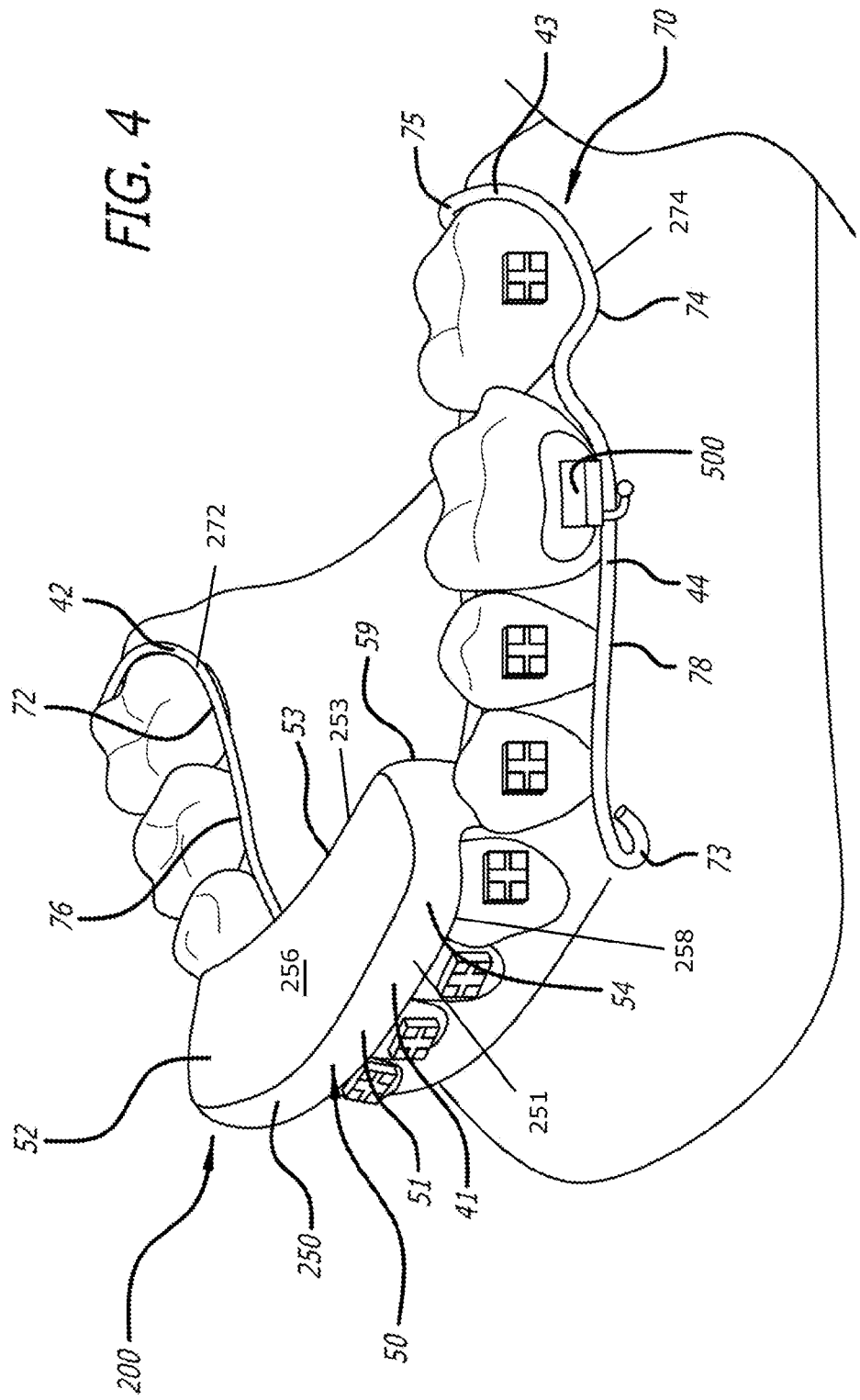
FIG. 4 is a front, left perspective view of an embodiment of the lower appliance portion of the present appliance on a model of a subject's teeth.

In the upper appliance portion 100, each of the right side wire 172 and the left side wire 174 of the upper appliance portion 100 extends posteriorly from the upper base 150 along the lingual side of the subject's upper teeth below the gingiva, is fitted around a rearmost tooth, and then extends anteriorly below the gingiva but above any brackets secured to the tooth on the buccal side, as can be seen for example in FIGS. 2 and 3. Likewise, in the lower appliance portion 200, each of the right side wire 272 and the left side wire 274 of the lower appliance portion 200 extends from the lower base 250 posteriorly along the lingual side of the subject's upper teeth below the gingiva, is fitted around a rearmost tooth, and then extends anteriorly above the gingiva but below any brackets secured to the tooth on the buccal side, as can be seen for example in FIGS. 4 and 5. Thus, on the lingual side, the wire 70 exits the base 50 and is designed to fit intimately against the lingual surface of all of the posterior teeth. The wire 70 preferably sits at the cemento-enamel junction (CEJ) and does not make contact with the gum tissue, sitting just above or below the tissue and between the gum tissue and any brackets on the user's teeth. The wire 70 is thereby held in place by the brackets.

Figure 5:
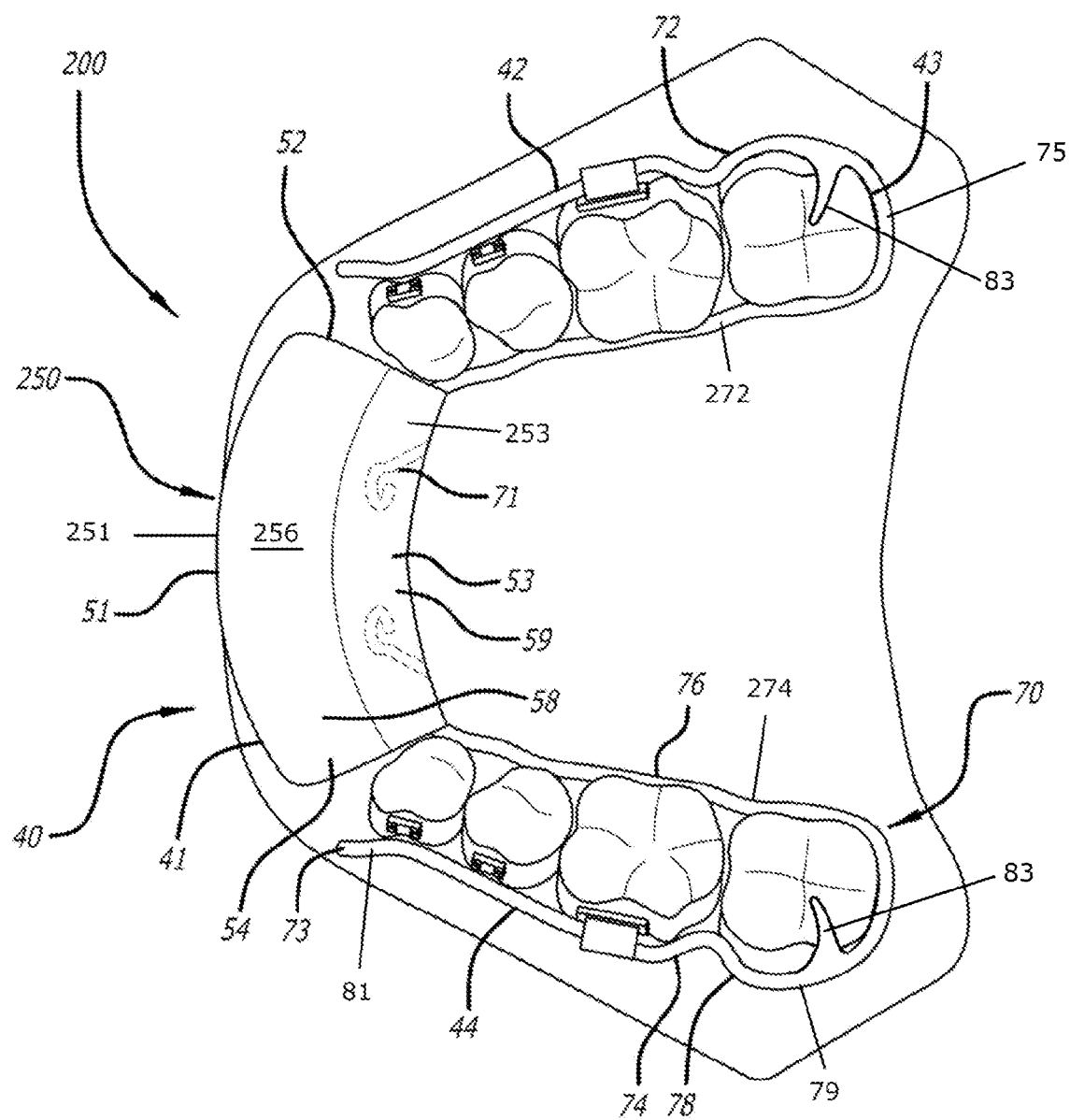
FIG. 5 is a top plan view of an embodiment of the present appliance on a model of a subject's teeth.

As seen in FIG. 5, one or more of the upper right side wire 172, upper left side wire 174, lower right side wire 272, and/or lower left side wire 274 can advantageously include a clasp 83. The clasp 83 comprises a flange, such as the wire portion which extends from the wires 272 and 274 shown in FIG. 5. Such wire portions extend medially from the buccal wire portion 78 or laterally from the lingual wire portion 76 and are adapted to extend over an occlusal surface of a tooth of the user. The clasps help to retain the appliance 10 and in particular the wires 70 on a user's teeth.

Each of the wires 70 is placed in intimate contact with a user's teeth so that the respective appliance portion can be retained on either the upper or lower jaw of the subject. In order to place the upper appliance portion 100 or lower appliance portion 200 on a user's teeth, the appliance portion 40 is placed in a user's mouth and the receptacle 60 of the base portion 50 is placed over the anterior teeth. The distal ends 73 of each of the wires 70 are then urged laterally outward so that the distal ends 73 and the buccal wire portions 76 extend further away from their respective lingual wire portions 78, i.e., so that the distance between the buccal wire portion 76 and the lingual wire portion 78 on each lateral side is increased, in order to allow the wire 70 to fit over any brackets. The wire 70 is then directed below brackets on the mandibular dentition or above brackets on the maxillary dentition, as the case may be, and the outward force on the wire is subsequently released, allowing the wire to return partially or completely to its pre-tensioned configuration. Preferably, the wires 70 contact the lingual and/or buccal surface of a plurality of a user's teeth under tension, in order to better retain the appliance portion 40 on the user's teeth, i.e., such that the wire remains under tension and exerts a force on at least some of the user's teeth so that it does not completely return to a pre-tensioned configuration while the appliance portion 40 is being worn. The wire 70 should have a modulus of elasticity which allows the wire 70 to be elastically bent in this way, so that after the appliance portion is positioned in the subject's mouth, the wire 70 will return to its conformation prior to being bent. The wire 70 is thus spring loaded, so that it can maintain its position above the brackets (in the upper appliance portion) or underneath the brackets (in the lower appliance portion 200). Once an appliance portion 40 is positioned in this way, the brackets of a user's braces operate to keep the appliance portion from being vertically displaced.

One of the advantages of the present appliance 10 is that it can be used during sleep to treat snoring or apnea without interfering with the ongoing orthodontic process of tooth and jaw movement. The wire 70 does not contact any brackets or any orthodontic wires, and therefore does not interfere with the tooth or jaw-moving forces being placed on a tooth, and is instead positioned between the bracket on a tooth and the gingiva above or below that bracket. A further feature for avoiding interference with the orthodontic process is the use of a thermoplastic material in at least the receptacle 60, as the conformation of such material can be changed over time to correspond to the changed positioning of the anterior teeth received by the receptacle 60. As discussed above, a user of the present appliance can soften the polymer material of the receptacle 60 on a regular basis, such as weekly, every other day, or more preferably daily, to accommodate movement of the anterior teeth covered by the receptacle 60 due to a user's use of orthodontic devices.

In order to position a user's jaws and thereby treat snoring and/or apnea, the upper appliance portion 100 includes a downwardly extending rigid projection 400 which extends downwardly from the lower side 158 of the upper base 150. The projection 400 has a proximal end 402, a distal end 404, an anterior surface 401, and a posterior surface 403. The proximal (upper) end 402 of the projection 400 is attached to the upper base 150, such as by being integrally molded with the upper base 150. As described below, the relative anterior-posterior positioning of the mandible with respect to the maxilla can be adjusted in some embodiments through use of inserts 300 which are attached to the lower base 250 of the lower appliance portion 200.

The distal end 404 of the projection 400 extends downwardly beyond the upper side 256 of the lower base 250 when the appliance 10 is worn by a subject, such that a portion of the distal end 404 of the projection 400 is positioned lingually with respect to the posterior side 253 of the lower base 250. The anterior surface 401 of the projection 400 thus touches or is adjacent to the posterior side 253 of the lower appliance portion 200 when the appliance 10 is worn by a user, and the projection 400 is positioned posteriorly with respect to the lower base 250. This positioning limits the posterior movement of the lower appliance portion 200 and hence also limits the movement of the user's lower jaw (mandible) with respect to the upper appliance portion 100 and the upper jaw (maxilla) of the user when the present appliance 10 is worn, thereby maintaining the user's jaws in an orientation conducive to preventing or ameliorating sleep apnea and/or snoring.

The projection 400 is preferably positioned in an anterior portion of the upper base 150, i.e., positioned in a relatively buccal orientation, such as below a user's upper incisors. This positioning provides space in the anterior palate area of a user's mouth, and encourages placement of the user's tongue in that area during sleep. This helps to avoid snoring and apnea, which may occur if a subject's tongue falls to the back of a user's mouth and blocks the subject's airway. Because the tongue is attached to the mandible, holding the mandible forward can prevent the tongue from dropping back into the airway.

Figure 6:
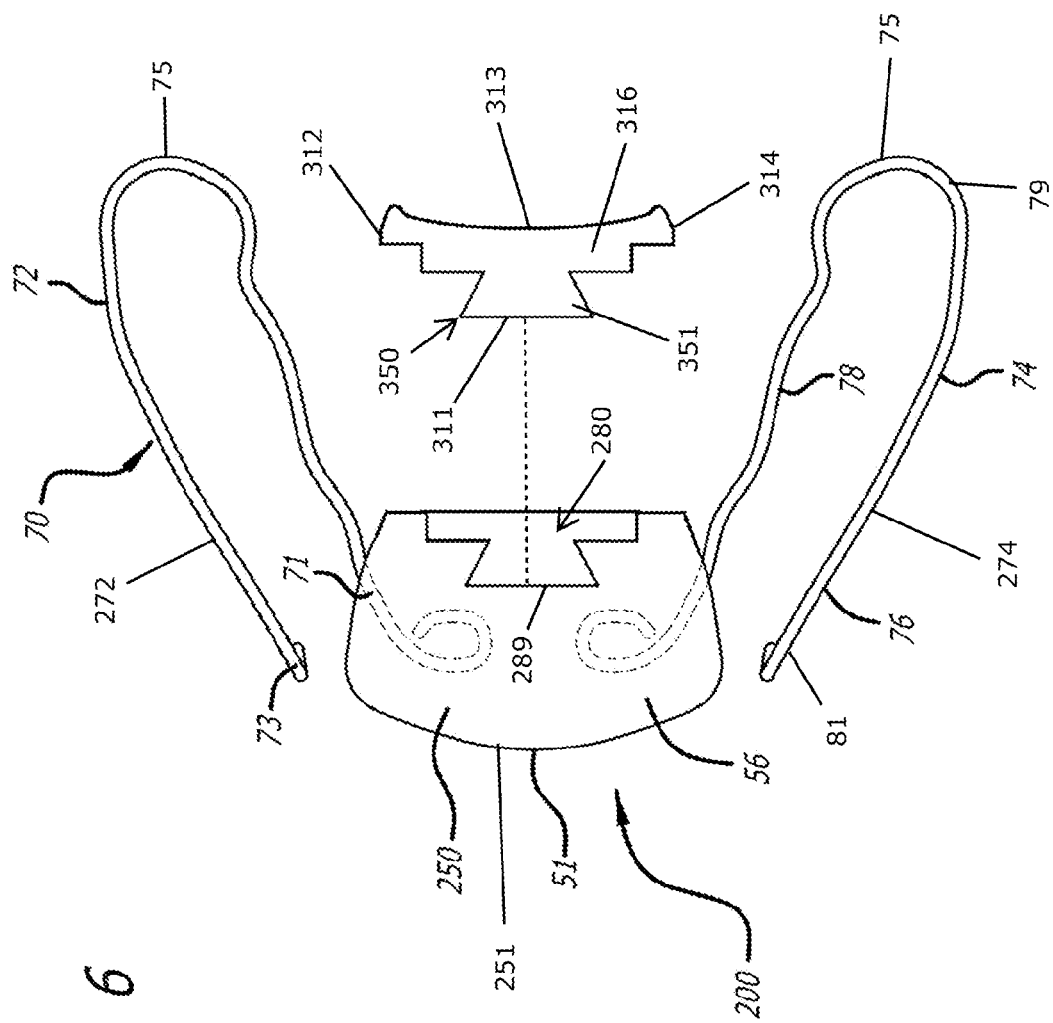
FIG. 6 is a top plan view of an embodiment of a lower appliance portion of the present appliance and an insert therefor.
Figure 7:
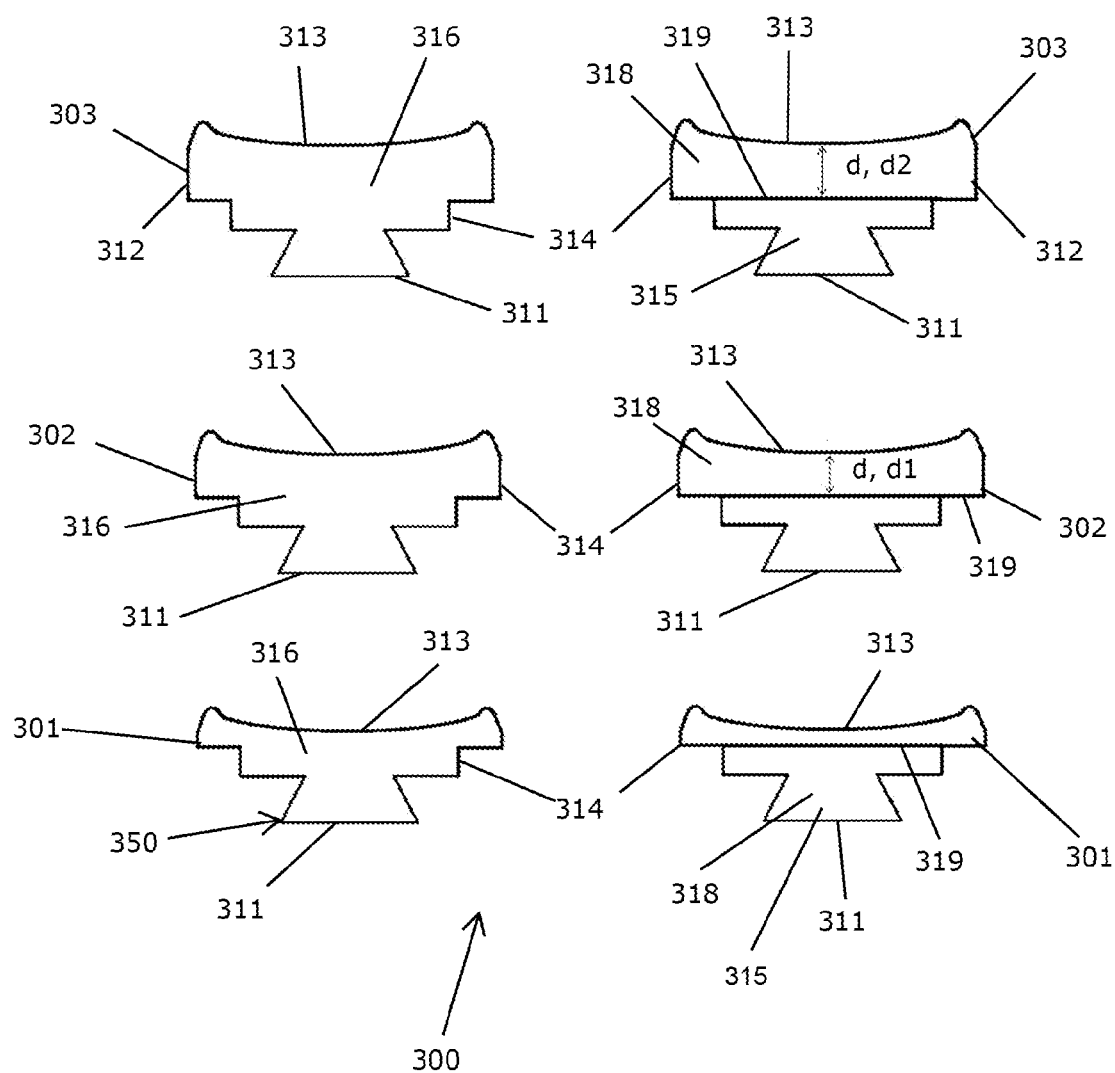
FIG. 7 is a plan view of the upper and lower sides of a plurality of inserts having different lengths for use with the appliance of FIG. 6.
Figure 8:
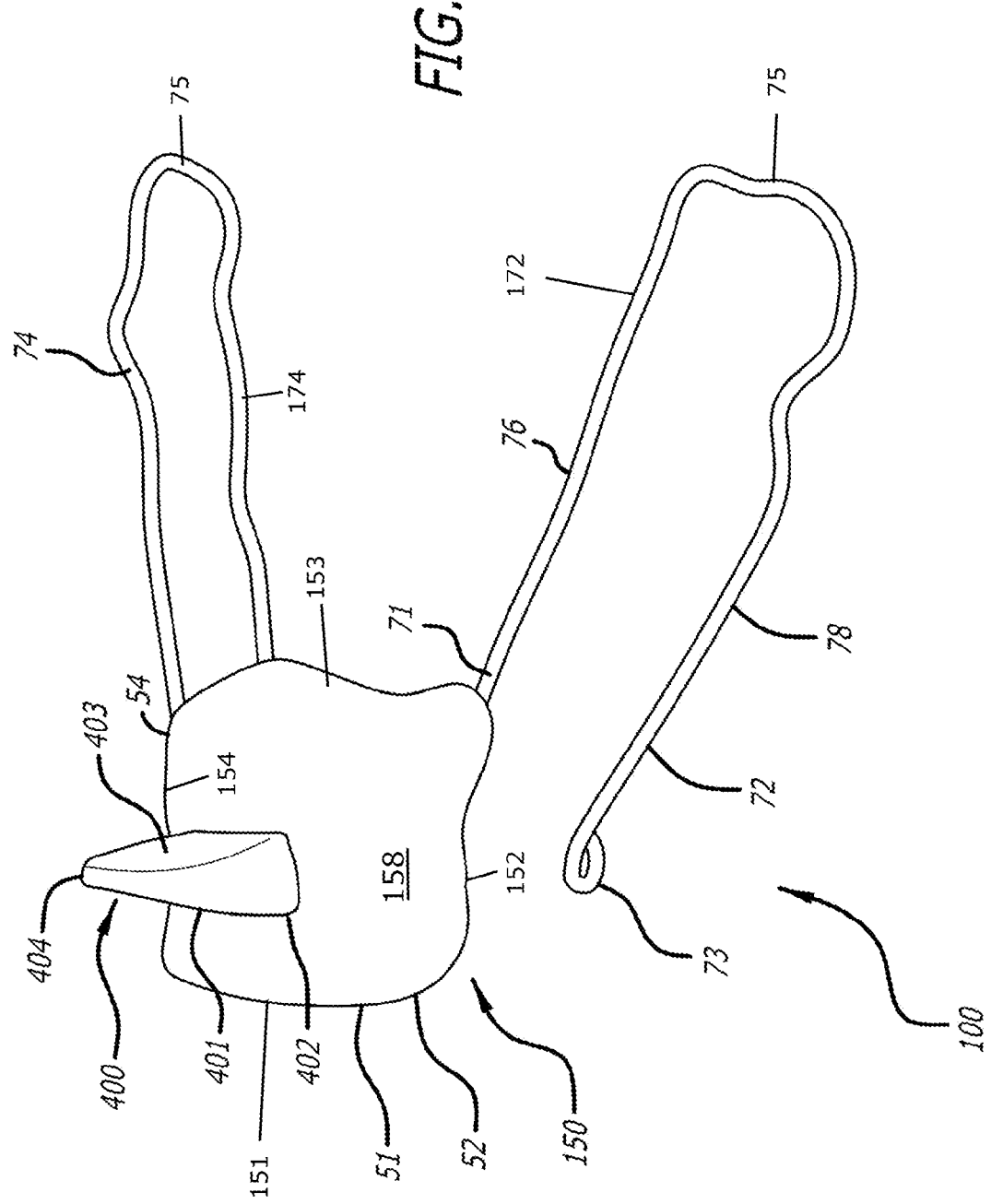
FIG. 8 is a left side perspective view of an embodiment of an upper appliance portion of the present appliance.

In order to provide different relative positioning of the upper and lower jaws of a patient, the base 250 of the lower appliance portion 200 can be provided with inserts 300 which connect to a posterior side 253 of the lower base 250 and extend posteriorly for different distances, as shown in FIGS. 6 and 7, in order to control the relative anterior-posterior positions of the maxilla and mandible of a user of the present appliance 10. The selection of an insert 300 having an appropriate posterior extent allows a lower appliance portion 200 to be fitted to a user and produce the correct positioning of the user's jaws. In prior appliance designs, inserts in an upper appliance tray have been used to adjust the position of downwardly extending projection relative to a lower appliance tray, however with this approach the inserts occupy space in an upper portion of the interior of a user's mouth and tend to block the tongue of the user. It is preferred that a user's tongue be positioned so that it touches a user's palate in the treatment of snoring or apnea, and the inserts 300 are therefore advantageously provided in the lower appliance portion 200 rather than the upper appliance portion 100, in order to encourage the user's tongue to rest on the front palate.

In order to fit the present appliance 10 to a subject, the inserts 300 are preferably reversibly securable (attachable) to the lower base portion 250, such as through mechanical connectors 350. In the embodiment illustrated in FIG. 6, connectors 350 extend anteriorly from inserts 300 and have attachment ends (in this case, anterior ends 351) adapted to be retained by the lower base portion 250. For example, mutually fitting locking elements in the anterior side 311 of an insert 300 can be configured to fit into and be retained by a matching element in the receiving portion 280 of the lower base 250 in order to retain the insert 300 on the lower base 250. In the illustrated example of FIG. 6, attachment end 351 of a connector 350 can engage with the mating portion 289 in the posterior side 253 of the base 250 of the lower appliance portion 200. The mating elements can be a tongue-and-groove arrangement as shown in FIGS. 6 and 7, with a tongue in the attachment end 351 sized to fit in a groove (mating portion) of receiving portion 280 in the posterior side 253 of the base 250. In this example, the sides of the wedge form an interference fit with the groove or recess of the receiving portion 280 in order to securely retain the insert 300. The insert 300 can in this case be formed from an elastomeric material, and the tongue can be formed with slightly larger dimensions than the recess so that when the tongue is urged into the recess it exerts an outward force that helps to retain it within the recess. Other known ways of attaching the insert 300 to the lower base 250 of the lower appliance portion 200 can also be used, for example the insert 300 can be attached to the lower appliance portion 200 with screws or other mechanical attachments.

The inserts 300 can control the anterior-posterior positions of the maxilla and mandible of a user by being formed with different posterior lengths. As shown in FIGS. 6 and 7, the inserts have a right side 312, left side 314, anterior side 311, and posterior side 313. In the illustrated embodiment, an anterior contact portion 315 of the lower side 318 of the insert 300 fits over an upper surface of the receiving portion 280, and a base-contacting anterior surface 319 contacts and covers the posterior side 253 of the lower base portion 250, so that when the insert 300 is attached to the lower base portion 250, the posterior side 313 of the insert 300 effectively becomes the posterior side 253 of the lower base portion 250 and contacts the anterior surface of the projection 400 of the upper base portion 150.

As seen in FIG. 7, the inserts 300 can vary in the extent to which their posterior sides extend posteriorly. In the illustrated embodiments, the difference in this extent is shown by the distance (d) between the base-contacting anterior surface 319 (adjacent the posterior side 253 of the lower base portion 250 when the insert is inserted into the lower base portion) and the posterior side 313 of the insert 300, specifically in a central portion of the posterior side 313 which will contact the projection 400 of the upper base portion 150. This distance increases from the relatively smaller distance of insert 301 to a larger (longer) distance of insert 302 and a larger distance still of insert 303, such that distance d2 of insert 303 is larger than the distance d1 of insert 302. Using insert 302 will position a user's mandible in a relatively more posterior position with respect to the maxilla as compared to longer insert 303 when the inserts are attached to the base 250, with insert 302 providing a jaw positioning between that of insert 301 and insert 303 due to its intermediate length (in the anterior-posterior direction) compared to that of inserts 301 and 303. The inserts can differ in length (i.e., distance, d) in increments of 1 mm (millimeter), increments of 0.5 mm, or increments of 0.25 mm, for example.

The base portions 50 of the present appliance 10 can be formed from a variety of orally compatible materials used to make orthodontic appliances, typically polymers such as acrylic. The wire portions of the appliance 10 can be formed from a variety of orthodontic metal wires, typically light orthodontic wires, which can be made for example from stainless steel or alloys of cobalt-chrome, nickel-titanium, or beta-titanium. The wires generally have diameters of between 0.016 and 0.050 inches (0.41 mm to 1.27 mm), preferably between about 0.020 and 0.040 inches (0.51 mm to 1 mm), and in one embodiment a diameter of about 0.030 inches (0.76 mm). The wires can have a modulus of elasticity of typical orthodontic wires, such as between about $14 \times 10^4$ MPa and $20 \times 10^4$ MPa. The wires must have sufficient resistance to bending to retain their shape during use, but also have sufficient elasticity to resume their shape following bending for insertion into or removal from a user's mouth.

The examples set forth herein are provided to illustrate certain concepts of the disclosure. The apparatus, devices, or components illustrated above may be configured to perform one or more of the methods, features, or steps described herein. Those of ordinary skill in the art will comprehend that these are merely illustrative in nature, and other examples may fall within the scope of the disclosure and the appended claims. Based on the teachings herein those skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structures in addition to or other than those set forth herein. The various features described above may also be combined in various ways. All possible combinations and sub-combinations are intended to fall within the scope of this disclosure. In addition, certain steps or features may be omitted in some implementations. All patents, patent publications, and other publications referred to herein are incorporated by reference in their entireties.

What is claimed is:

1. A sleep appliance for use with orthodontic braces, comprising:
   (1) an upper appliance portion for use on maxillary dentition of a user of the appliance, comprising:
      (a) an upper base portion having a right side, a left side, an anterior side, a posterior side, an upper side, and a lower side;
      (b) an upper right side wire having a proximal end, a distal end, a lingual wire portion, a buccal wire portion, and a medial portion, wherein:
         (i) the proximal end of the upper right side wire is attached to the right side of the upper base portion;
         (ii) the lingual wire portion of the upper right side wire extends posteriorly from the proximal end to the medial portion, the medial portion of the upper right side wire extends laterally, and the buccal wire portion of the upper right side wire extends from the medial portion anteriorly to the distal end; and
         (iii) the upper right side wire is adapted to fit between brackets of orthodontic braces affixed to teeth of the user of the appliance and gum tissue of the user;
      (c) an upper left side wire having a proximal end, a distal end, a lingual wire portion, a buccal wire portion, and a medial portion, wherein:
         (i) the proximal end of the upper left side wire is attached to the left side of the upper base portion;
         (ii) the lingual wire portion of the upper left side wire extends posteriorly from the proximal end to the medial portion, the medial portion of the upper left side wire extends laterally, and the buccal wire portion of the upper left side wire extends from the medial portion anteriorly to the distal end; and
         (iii) the upper left side wire is adapted to fit between brackets of orthodontic braces affixed to teeth of the user of the appliance and gum tissue of the user;
      (d) an upper receptacle having an upper surface, wherein the upper receptacle comprises a thermoplastic material; and
      (e) a downwardly extending projection having a proximal end, a distal end, an anterior surface, and a posterior surface, wherein the projection is attached to and extends downwardly from the lower side of the upper base portion; and
   (2) a lower appliance portion for use on mandibular dentition of a user of the appliance, comprising:
      (a) a lower base portion having a right side, a left side, an anterior side, a posterior side, an upper side, and a lower side;
      (b) a lower right side wire having a proximal end, a distal end, a lingual wire portion, a buccal wire portion, and a medial portion, wherein:
         (i) the proximal end of the lower right side wire is attached to the right side of the lower base portion;
         (ii) the lingual wire portion of the lower right side wire extends posteriorly from the proximal end to the medial portion, the medial portion of the lower right side wire extends laterally, and the buccal wire portion of the lower right side wire extends from the medial portion anteriorly to the distal end; and
         (iii) the lower right side wire is adapted to fit between brackets of orthodontic braces affixed to teeth of the user of the appliance and gum tissue of the user;
      (c) a lower left side wire having a proximal end, a distal end, a lingual wire portion, a buccal wire portion, and a medial portion, wherein:
         (i) the proximal end of the lower left side wire is attached to the left side of the lower base portion;
         (ii) the lingual wire portion of the lower left side wire extends posteriorly from the proximal end to the medial portion, the medial portion of the lower left side wire extends laterally, and the buccal wire portion of the lower left side wire extends from the medial portion anteriorly to the distal end; and
         (iii) the lower left side wire is adapted to fit between brackets of orthodontic braces affixed to teeth of the user of the appliance and gum tissue of the user; and
      (d) a lower receptacle having a lower surface, wherein the lower receptacle comprises a thermoplastic material,
   wherein the anterior surface of the projection is adapted to contact the posterior side of the lower base portion when the appliance is in use, thereby limiting anterior movement of the upper appliance portion with respect to the lower appliance portion, and
   wherein the thermoplastic material can be reversibly deformed in order to accommodate changing tooth positions of the teeth of the user.

2. The sleep appliance of claim 1, wherein the lower appliance portion further comprises:
   an insert having a right side, a left side, an anterior side, a posterior side, an upper side, and a lower side; and
   a receiving portion in the lower base portion, wherein the insert is configured to be secured to the receiving portion.

3. The sleep appliance of claim 2, further comprising a plurality of inserts, wherein the posterior side of each of the plurality of inserts extends posteriorly by a different distance when retained in the receiving portion, and wherein each of the plurality of inserts is reversibly securable to the lower appliance portion.

4. The sleep appliance of claim 3, wherein distance by which each of the inserts extends posteriorly is different by between 0.5 mm and 1.0 mm.

5. The sleep appliance of claim 2, wherein the anterior side of the insert and the posterior side of the lower appliance portion are provided with mutually fitting locking elements in order to secure the insert to the receiving portion.

6. The sleep appliance of claim 5, wherein the mutually fitting locking elements are tongue-and-groove locking elements.

7. The sleep appliance of claim 1, wherein the upper right side wire, upper left side wire, lower right side wire, and lower left side wire can be elastically deformed and are adapted to contact a user's teeth under tension.

8. The sleep appliance of claim 1, wherein the upper base portion and lower base portion are formed from a thermoplastic material.

9. The sleep appliance of claim 1, wherein the upper base portion and lower base portion further comprise a hard plastic material.

10. The sleep appliance of claim 1, further comprising a clasp extending from one or more of the upper right side wire, upper left side wire, lower right side wire, and/or lower left side wire, wherein the clasp extends medially from the buccal wire portion or laterally from the lingual wire portion and is adapted to extend over an occlusal surface of a tooth of the user.

11. A method of treating snoring or sleep apnea, comprising the step of applying the sleep appliance of claim 1 to a subject in need thereof.

12. The method of claim 11, further comprising the steps of:
(a) heating the upper appliance portion in order to soften the thermoplastic material of the upper appliance portion and taking an impression of the subject's anterior maxillary dentition;
(b) heating the lower appliance portion in order to soften the thermoplastic material of the lower appliance portion and taking an impression of the subject's anterior mandibular dentition;
(c) repeating steps (a) and (b) every 1-3 days.

* * * * *